(12) United States Patent
Saito

(10) Patent No.: US 10,939,856 B2
(45) Date of Patent: Mar. 9, 2021

(54) PROCESSOR DEVICE, ENDOSCOPE SYSTEM, AND IMAGE PROCESSING METHOD

(71) Applicant: FUJIFILM Corporation, Tokyo (JP)

(72) Inventor: Takaaki Saito, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 345 days.

(21) Appl. No.: 15/969,779

(22) Filed: May 3, 2018

(65) Prior Publication Data

US 2018/0242893 A1  Aug. 30, 2018

Related U.S. Application Data

(63) Continuation of application No. PCT/JP2016/077502, filed on Sep. 16, 2016.

(30) Foreign Application Priority Data

Nov. 6, 2015 (JP) .............................. JP2015-218343

(51) Int. Cl.
*A61B 5/1455* (2006.01)
*A61B 1/00* (2006.01)
(Continued)

(52) U.S. Cl.
CPC ............ *A61B 5/14552* (2013.01); *A61B 1/00* (2013.01); *A61B 1/00009* (2013.01);
(Continued)

(58) Field of Classification Search
CPC ......... A61B 5/14552; A61B 1/00; A61B 1/04; A61B 5/0084; A61B 5/14503;
(Continued)

(56) References Cited

U.S. PATENT DOCUMENTS

2006/0241349 A1  10/2006  Gono
2008/0024868 A1  1/2008  Okamura et al.
(Continued)

FOREIGN PATENT DOCUMENTS

EP  1576920  9/2005
EP  2850993  3/2015
(Continued)

OTHER PUBLICATIONS

"Search Report of Europe Counterpart Application", dated Oct. 19, 2018, p. 1-p. 7.
(Continued)

*Primary Examiner* — Eric F Winakur
*Assistant Examiner* — Abid A Mustansir
(74) *Attorney, Agent, or Firm* — JCIPRNET

(57) ABSTRACT

Provided are a processor device, an endoscope system, and an image processing method capable of discovering not only a lesion in which scattering particles according to a specific scattering model are present but also various lesions. A processor device 16 includes an image acquisition unit 54 that acquires images of three wavelength ranges of a blue wavelength range, a green wavelength range, and a red wavelength range; a scattering characteristic amount calculation unit 71 that calculates a scattering characteristic amount representing a scattering characteristic of an observation object, using the images of the three wavelength ranges; and an image generation unit 74 that generates a scattering characteristic amount image representing a distribution of the scattering characteristic amount.

18 Claims, 9 Drawing Sheets

(51) Int. Cl.
*A61B 1/04* (2006.01)
*G02B 23/24* (2006.01)
*A61B 5/00* (2006.01)
*A61B 5/145* (2006.01)
*A61B 1/06* (2006.01)

(52) U.S. Cl.
CPC ............ *A61B 1/00188* (2013.01); *A61B 1/04* (2013.01); *A61B 1/0638* (2013.01); *A61B 1/0646* (2013.01); *A61B 1/0684* (2013.01); *A61B 5/0084* (2013.01); *A61B 5/14503* (2013.01); *A61B 5/14551* (2013.01); *G02B 23/24* (2013.01); *A61B 1/041* (2013.01)

(58) Field of Classification Search
CPC ............ A61B 5/14551; A61B 1/00009; A61B 1/00188; A61B 1/0638; A61B 1/0646; A61B 1/0684; A61B 1/041; G02B 23/24
See application file for complete search history.

(56) References Cited

U.S. PATENT DOCUMENTS

| | | | |
|---|---|---|---|
| 2012/0120487 A1 | 5/2012 | Akiyama et al. | |
| 2014/0066733 A1* | 3/2014 | Saito | A61B 1/00009 600/339 |
| 2015/0145978 A1 | 5/2015 | Chiba | |
| 2015/0182206 A1 | 7/2015 | Hendriks et al. | |

FOREIGN PATENT DOCUMENTS

| | | |
|---|---|---|
| JP | 2004202217 | 7/2004 |
| JP | 2013240401 | 12/2013 |
| JP | 2014046150 | 3/2014 |
| JP | 2015527899 | 9/2015 |

OTHER PUBLICATIONS

Erik H. Lindsley, et al, "The hyperspectral imaging endoscope: a new tool for in vivo cancer detection," Proceedings of SPIE—The International Society for Optical Engineering, vol. 5322, Jul. 2004, pp. 1-9.

"International Search Report (Form PCT/ISA/210) of PCT/JP2016/077502," dated Nov. 22, 2016, with English translation thereof, pp. 1-5.

"International Preliminary Report on Patentability (Form PCT/IPEA/409) of PCT/JP2016/077502," completed on Oct. 31, 2017, with English translation thereof, pp. 1-7.

* cited by examiner

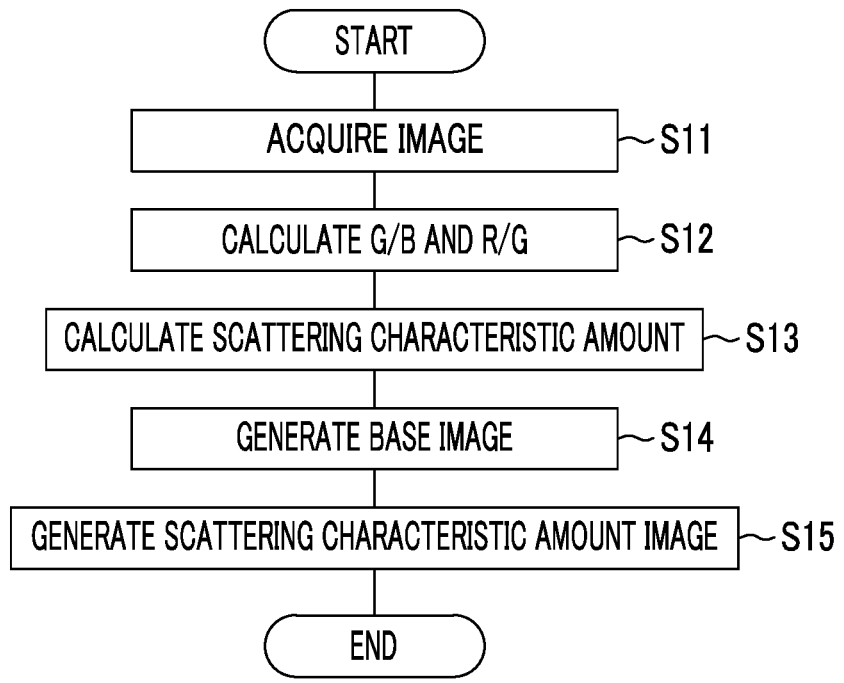
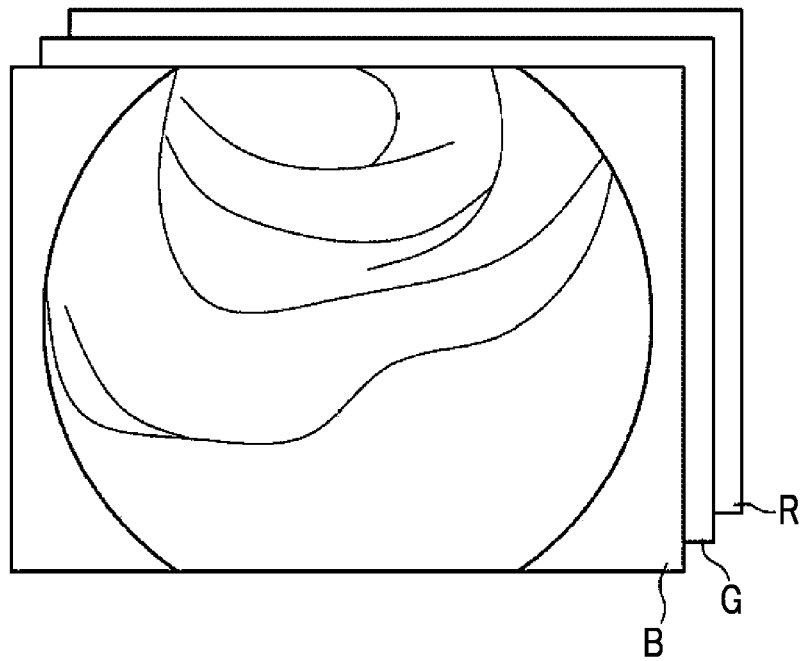

PROCESSOR DEVICE, ENDOSCOPE SYSTEM, AND IMAGE PROCESSING METHOD

CROSS-REFERENCE TO RELATED APPLICATIONS

This application is a Continuation of PCT International Application No. PCT/JP2016/077502 filed on Sep. 16, 2016, which claims priority under 35 U.S.C § 119(a) to Japanese Patent Application No. 2015-218343 filed on Nov. 6, 2015. Each of the above application(s) is hereby expressly incorporated by reference, in its entirety, into the present application.

BACKGROUND OF THE INVENTION

1. Field of the Invention

The present invention relates to a processor device, an endoscope system, and an image processing method that images characteristics regarding light scattering of an observation object.

2. Description of the Related Art

In the medical field, it is general to perform diagnosis using endoscope systems including a light source device, an endoscope, and a processor device. Particularly, endoscope systems for obtaining an image in which specific tissues or structures, such as blood vessels or duct structures, are enhanced simply not only by naturally observing an observation object but also by devising the wavelength of illumination light or by performing processing, such as spectrum estimation processing, on an image obtained by imaging the observation object have become widespread.

Additionally, an endoscope system that can discover a lesion by imaging a light-scattering characteristic of an observation object rather than enhancing specific tissue and structure is also known (JP2004-202217A). The endoscope system of JP2004-202217A acquires images of three blue wavelength ranges having wavelengths of 420 nm, 450 nm, and 470 nm, and estimates the spectroscopic spectrum of the observation object for each pixel, using these images. Then, the amount of characteristic regarding light scattering, such as the average or standard deviation of particle diameters of the observation object is calculated from the estimated spectroscopic spectrum. In a case where the spectroscopic spectrum is estimated, it is assumed that the scattering particles in the observation object have a size approximately equal to the wavelengths and follow the so-called Mie scattering.

SUMMARY OF THE INVENTION

As described above, the endoscope system of JP2004-202217A uses the light beams of the three blue wavelength ranges, and calculates the amount of characteristic regarding the light scattering on the assumption that the scattering particles which are present in the lesion follow the Mie scattering. For this reason, the lesion that can be discovered in the images provided by the endoscope system of JP2004-202217A is basically limited to the lesion in which the scattering particles which are present in the lesion follow the Mie scattering.

Additionally, it is true that scattering particles which are present in many lesions have the characteristic to follow the Mie scattering. However, this is after the lesions have progressed to some extent. In an extremely early stage of generation of a lesion, scattering particles which are present in the lesion are not always developed into the size following the Mie scattering. Hence, as long as it is assumed that the scattering particles present in the lesion follow the Mie scattering, the lesion in such an extremely early stage of generation cannot be discovered.

An object of the invention is to provide a processor device, an endoscope system, and an image processing method capable of discovering not only a lesion in which scattering particles according to a specific scattering model are present but also various lesions.

A processor device of the invention comprises an image acquisition unit that acquires images of three wavelength ranges of a blue wavelength range, a green wavelength range, and a red wavelength range; a scattering characteristic amount calculation unit that calculates a scattering characteristic amount representing a scattering characteristic of an observation object, using the images of the three wavelength ranges; and an image generation unit that generates a scattering characteristic amount image representing a distribution of the scattering characteristic amount.

It is preferable that the blue wavelength range, the green wavelength range, and the red wavelength range include equal absorption wavelength ranges in which light absorption coefficients of oxyhemoglobin and reduced hemoglobin is equal to each other.

It is preferable that the scattering characteristic amount calculation unit acquires color information from the images of the three wavelength ranges, and calculates the scattering characteristic amount, using the color information.

It is preferable that the scattering characteristic amount calculation unit calculates a ratio or difference between the images of the three wavelength ranges as the color information, and calculates the scattering characteristic amount, using the calculated ratio or difference.

It is preferable that the scattering characteristic amount calculation unit calculates the scattering characteristic amount, using the ratio or difference between the image of the red wavelength range and the image of the green wavelength range, and the ratio or difference between the image of the green wavelength range and the image of the blue wavelength range.

It is preferable that the scattering characteristic amount calculation unit calculates a parameter representing wavelength dependability of a scattering coefficient of the observation object as the scattering characteristic amount.

It is preferable that the scattering characteristic amount calculation unit calculates a scattering characteristic amount "b" corresponding to the color information in a color information space which is formed with the color information as axes and in which a relationship among a wavelength "λ", a scattering coefficient $\mu_s$ of the observation object, and the scattering characteristic amount "b" is defined by Expression 1.

$$\mu_s \propto \lambda^{-b} \qquad \text{Expression 1:}$$

It is preferable that the image acquisition unit acquires an image of a fourth wavelength range having a difference between the light absorption coefficient of the hemoglobin and the light absorption coefficient of the reduced hemoglobin as compared to the three wavelength ranges, the processor device further comprises an oxygen saturation calculation unit that calculates an oxygen saturation of the observation object, using the image of the fourth wavelength range, and the image generation unit generates the scattering characteristic amount image representing a distribution of the oxygen saturation as well as the distribution of the scattering characteristic amount.

It is preferable that the image generation unit sets ranges to the scattering characteristic amount and the oxygen saturation, respectively, and generates the scattering characteristic amount image in which a portion is present within a range where the scattering characteristic amount is set and a range where the oxygen saturation is set is enhanced.

It is preferable that the image generation unit compares the scattering characteristic amount with a first threshold value, and generates the scattering characteristic amount image in which a portion in which the scattering characteristic amount is equal to or less than the first threshold value is enhanced.

It is preferable that the image generation unit compares the oxygen saturation with a second threshold value, and generates the scattering characteristic amount image in which a portion in which the oxygen saturation is equal to or less than the second threshold value is enhanced.

An endoscope system of the invention comprises an image acquisition unit that acquires images of three wavelength ranges of a blue wavelength range, a green wavelength range, and a red wavelength range; a scattering characteristic amount calculation unit that calculates a scattering characteristic amount representing a scattering characteristic of an observation object, using the images of the three wavelength ranges; and an image generation unit that generates a scattering characteristic amount image representing a distribution of the scattering characteristic amount.

An image processing method of the invention comprises a step of acquiring images of three wavelength ranges of a blue wavelength range, a green wavelength range, and a red wavelength range with an image acquisition unit; a step of calculating a scattering characteristic amount representing a scattering characteristic of an observation object, using the images of the three wavelength ranges, with a scattering characteristic amount calculation unit; and a step of generating a scattering characteristic amount image representing a distribution of the scattering characteristic amount with an image generation unit.

According to the processor device, the endoscope system, and the image processing method of the invention, the images of the three wavelength ranges of the blue wavelength range, the green wavelength range, and the red wavelength range are acquired, and the scattering characteristic of the observation object are calculated using these. Thus, it is possible to discover not only a lesion in which scattering particles following a specific scattering model are present but also various lesions.

BRIEF DESCRIPTION OF THE DRAWINGS

FIG. 7 is a flowchart illustrating a flow of operation in a scattering characteristic amount observation mode.
FIG. 8 is an image acquired by an image acquisition unit.

DESCRIPTION OF THE PREFERRED EMBODIMENTS

First Embodiment

Figure 1:
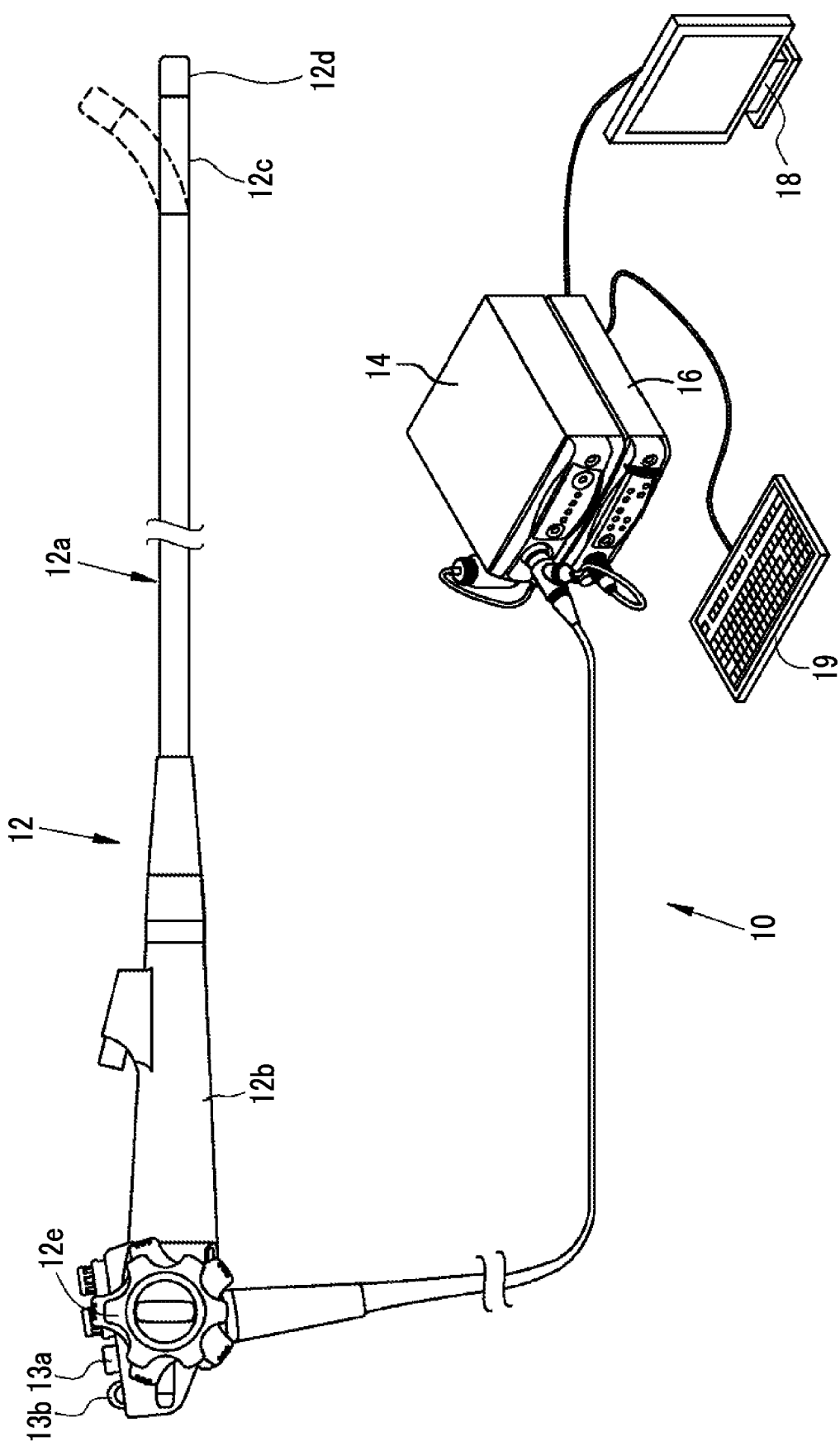
FIG. 1 is an external view of an endoscope system.

As illustrated in FIG. 1, an endoscope system 10 has an endoscope 12, a light source device 14, a processor device 16, a monitor 18 (display unit), and a console 19. The endoscope 12 is optically connected to the light source device 14, and is electrically connected to the processor device 16. The endoscope 12 has an insertion part 12a to be inserted into a subject, an operating part 12b provided at a base end portion of the insertion part 12a, and a bending part 12c and a distal end part 12d provided on a distal end side of the insertion part 12a. By operating an angle knob 12e of the operating part 12b, the bending part 12c makes a bending motion. The distal end part 12d is directed in a desired direction by this bending motion.

Additionally, the operating part 12b is provided with a mode changeover switch 13a and a zooming operation part 13b other than the angle knob 12e. The mode changeover switch 13a is used for switching operation in an observation mode. The endoscope system 10 has two observation modes of a normal observation mode and a scattering characteristic amount observation mode. The normal observation mode is an observation mode in which white light is radiated to image an observation object and a natural-tone image (hereinafter referred to as a normal image) is displayed on the monitor 18. The scattering characteristic amount observation mode is an observation mode in which a scattering characteristic amount representing the scattering characteristic of an observation object is calculated using images of the three wavelength ranges obtained by imaging the observation object, using light of the three wavelength ranges of a blue wavelength range, a green wavelength range, and a red wavelength range and a scattering characteristic amount image representing the distribution of the scattering characteristic amount is generated and displayed.

The processor device 16 is electrically connected to the monitor 18 and the console 19. The monitor 18 outputs and displays the images in the respective observation modes, image information accompanying the images, and the like. The console 19 functions as a user interface that receives an input operation, such as function setting. In addition, an external recording unit (not illustrated) that records the images, the image information, and the like may be connected to the processor device 16.

Figure 2:
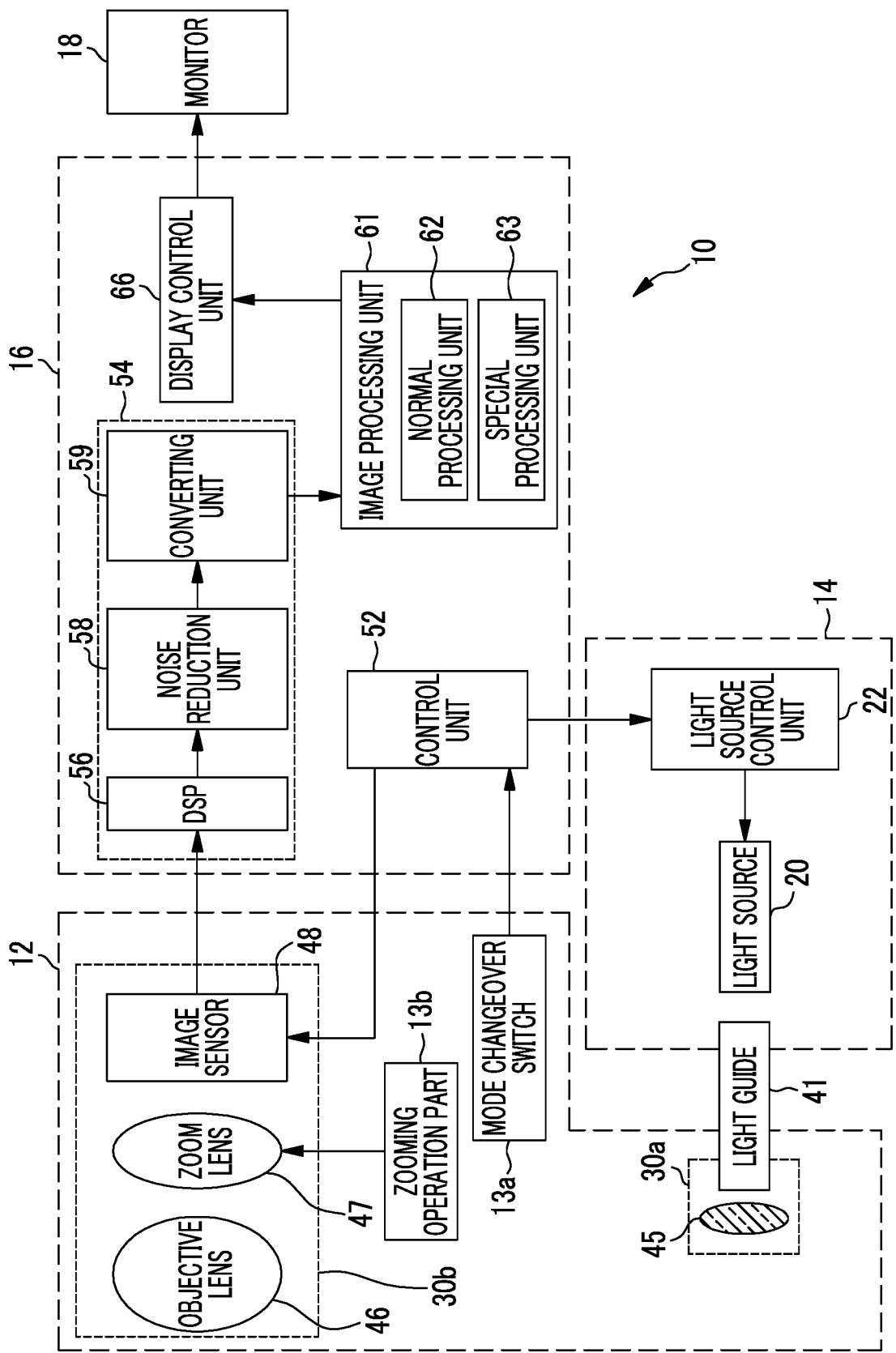
FIG. 2 is a block diagram of an endoscope system.

As illustrated in FIG. 2, the light source device 14 includes a light source 20 that emits illumination light, and a light source control unit 22 that controls driving of the light source 20.

The light source 20 is constituted of, for example, light emitting diodes (LEDs) in a plurality of colors, and emits white light in the normal observation mode. Additionally, in the scattering characteristic amount observation mode, the light beams of the three wavelength ranges of the blue wavelength range, the green wavelength range, and the red wavelength range are sequentially emitted. More specifically, all of the three wavelength ranges of the blue wavelength range, the green wavelength range, and the red wavelength range include an absorption wavelength range in which the light absorption coefficients of oxyhemoglobin and reduced hemoglobin are substantially equal to each other. A wavelength range of a light beam emitted in the scattering characteristic amount observation mode by the light source 20 is used as a wavelength range including an equal absorption wavelength range in order to reduce the influence (error or the like) by a difference in light absorption amount between the oxyhemoglobin and the reduced hemoglobin in a case where calculating the scattering characteristic amount.

Figure 3:
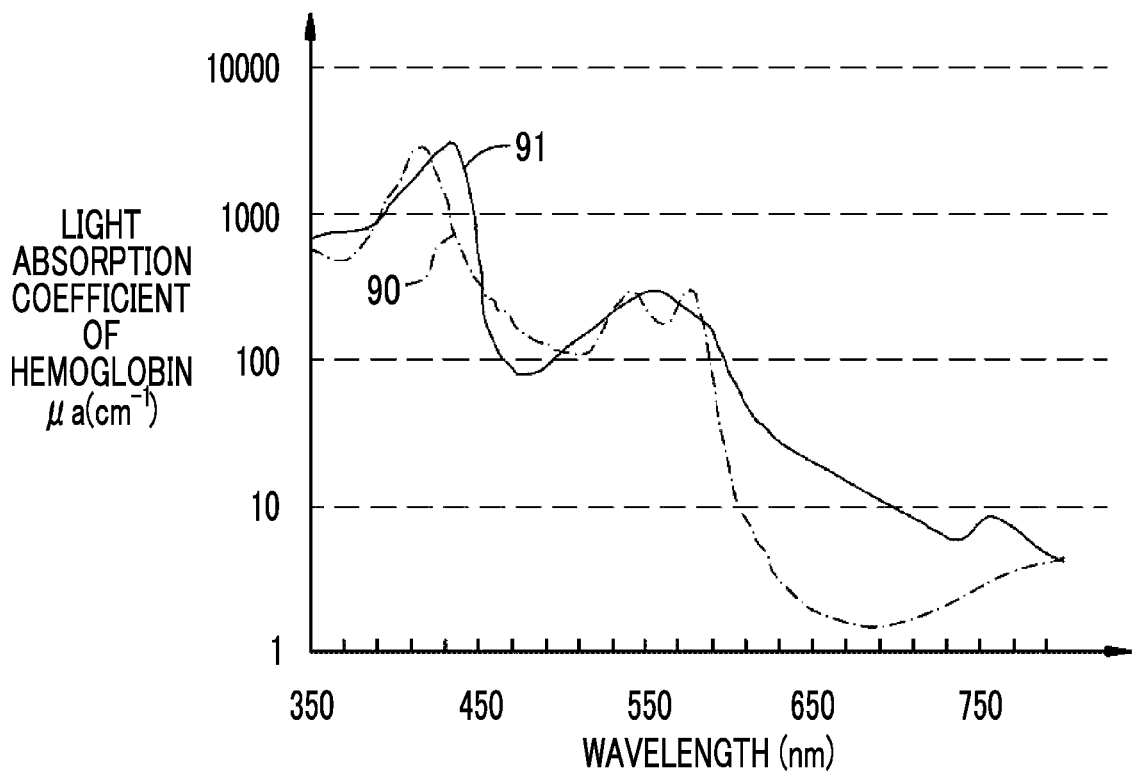
FIG. 3 is a graph illustrating the light absorption coefficient of hemoglobin.

As illustrated in FIG. 3, there is a difference in wavelength dependability between an light absorption coefficient $\mu_a$ (graph 90) of the oxyhemoglobin and an light absorption coefficient $\mu_a$ (graph 91) of the reduced hemoglobin. However, there are a plurality of equal absorption wavelength ranges in which these light absorption coefficients intersect each other and the light absorption coefficients $\mu_a$ of the oxyhemoglobin and the reduced hemoglobin becomes substantially equal to each other. For example, a wavelength range of 450±10 nm is a so-called blue wavelength range, and is an equal absorption wavelength range. Additionally, a wavelength range of 540±10 nm is a so-called green wavelength range, and is an equal absorption wavelength range. In FIG. 3, a difference between a graph 90 and a graph 91 is great in the so-called red wavelength range. This is because a vertical axis is expressed by the logarithm. Since the light beam of the red wavelength range has extremely small light absorption amounts of the oxyhemoglobin and the reduced hemoglobin compared to the light beam of the blue wavelength range or the light beam of the green wavelength range, the red wavelength range is regarded as a substantially equal absorption wavelength range. From these points, in the present embodiment, the light source 20 emits a light beam of the blue wavelength range of 450±10 nm, a light beam of the green wavelength range of 540±10 nm, and a light beam of the red wavelength range of 620±10 nm in the scattering characteristic amount observation mode. In addition, in the present embodiment, as described above, the three wavelength ranges of the blue wavelength range, the green wavelength range, and the red wavelength range are wavelength ranges that substantially coincide with equal absorption wavelength ranges, these three wavelength ranges do not need to strictly coincide with the equal absorption wavelength ranges. For example, the blue wavelength range may include the equal absorption wavelength range, and may be brought into a state where there is almost no difference in light absorption amount between the oxyhemoglobin and the reduced hemoglobin, as a whole. In a case where the blue wavelength range is a wavelength range including the equal absorption wavelength range, this condition is satisfied easily. The same applies to the green wavelength range and the red wavelength range.

In addition, as the light source 20, a laser diode (LD), a fluorescent body, or a lamp, such as a xenon lamp, can be used instead of the LED. The light source 20 includes a band limit filter that limits the wavelength range of a light beam to be emitted in a case where necessary. Additionally, in the present embodiment, the light source 20 sequentially emits the light beams of the three wavelength ranges in the scattering characteristic amount observation mode. However, these light beams may be emitted simultaneously.

The light source control unit 22 controls the colors (wavelength ranges) of the light beams emitted from the light source 20, a spectroscopic spectrum, light emission timing, light emission amount, and the like. For example, the light source control unit 22 switches the light emitted from the light source 20 to the white light for the normal observation modes, and the light beams of the three wavelength ranges for the scattering characteristic amount observation mode by the operation of a mode changeover switch 13a.

The light emitted from the light source 20 enters a light guide 41. The light guide 41 is built in the endoscope 12 and a universal cord (a cord that connects the endoscope 12, and the light source device 14 and the processor device 16 to each other), and propagates the illumination light to the distal end part 12d of the endoscope 12. In addition, multimode fiber can be used as the light guide 41. As an example, a fine-diameter fiber cable of which the core diameter is 105 μm, the clad diameter is 125 μm, and a diameter including a protective layer used as an outer cover is ϕ0.3 mm to 0.5 mm can be used.

The distal end part 12d of the endoscope 12 is provided with an illumination optical system 30a and an imaging optical system 30b. The illumination optical system 30a has an illumination lens 45, and the illumination light is radiated to the observation object via the illumination lens 45. The imaging optical system 30b has an objective lens 46, a zoom lens 47, and an image sensor 48. The image sensor 48 images the observation object via the objective lens 46 and the zoom lens 47, using reflected light, scattered light, or the like (including fluorescence emitted from the observation object, fluorescence emitted from medicine administered to the observation object, or the like) of the illumination light that returns from the observation object. In addition, the zoom lens 47 is moved by the operation of the zooming operation part 13b, and magnifies or reduces the observation object to be imaged by the image sensor 48.

The image sensor 48 is a color sensor of a primary color system having three kinds of pixels corresponding to a blue pixel (B pixel) provided with a blue (B) color filter, a green pixel (G pixel) provided with a green (G) color filter, and a red pixel (R pixel) provided with a red (R) color filter. For this reason, in a case where the observation object is imaged by the image sensor 48, three kinds of images of a blue image (B image), a green image (G image), and a red image (R image), are obtained.

In addition, although the image sensor 48 is a color sensor of a primary color system, a color sensor of a complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images in the respective colors obtained in a case where the color sensor of the complementary color system is used can be converted into the B image, the G image, and the R image that are the same as those in the above embodiment. Additionally, a monochrome sensor having no color filter can also be used as the image sensor 48. In a case where the monochrome sensor is used as image sensor 48, the B image, the G image, and the R image can be obtained, for example, by sequentially radiating the light beams of the blue wavelength range, the green wavelength range, and the red wavelength range to the observation object to image the observation object.

The processor device 16 includes a control unit 52, an image acquisition unit 54, an image processing unit 61, and a display control unit 66. The control unit 52 receives input of a mode switching signal from the mode changeover switch 13a, controls the light source control unit 22 and the image sensor 48, and switches between the observation modes. Specifically, the control unit 52 performs designation of the type and the light quantity of the illumination light for the light source control unit 22, control of the length of the exposure time of the image sensor 48 and the gain at the time of image output therefrom, synchronous control of the switching timing of the imaging frames and the illumination light, and the like.

The image acquisition unit 54 acquires images in respective colors from the image sensor 48. In the case of the normal observation mode, three-color spectrum images of the B image, the G image, and the R image obtained by radiating the white light to the observation object are acquired from the image sensor 48. Similarly, in the scattering characteristic amount observation mode, three-color spectrum images respectively corresponding to the light beams of the three wavelength ranges emitted from the light source 20 are acquired from the image sensor 48. However, the images acquired by the image acquisition unit 54 in the scattering characteristic amount observation mode are a B image captured by radiating a light beam of a blue and equal absorption wavelength range to the observation object, a G image captured by radiating a light beam of a green and equal absorption wavelength range to the observation object, and an R image captured by radiating a light beam of a red and equal absorption wavelength range to the observation object.

The image acquisition unit 54 has a digital signal processor (DSP) 56, a noise reduction unit 58, and a converting unit 59, and performs various kinds of processing on an image acquired by these units.

The DSP 56 performs various kinds of processing, such as defect correction processing, offset processing, gain correction processing, linear matrix processing, gamma conversion processing, demosaicing processing, and YC conversion processing, on the acquired image.

The defect correction processing is the processing of correcting the pixel value of a pixel corresponding to a defective pixel of the image sensor 48. The offset processing is the processing of removing a dark current component from the image subjected to the defect correction processing, and setting an accurate zero level. The gain correction processing is the processing of adjusting a signal level by multiplying the image subjected to the offset processing by a gain. The linear matrix processing is the processing of enhancing color reproducibility on the image subjected to the offset processing, and the gamma conversion processing is the processing of adjusting the brightness or saturation of the image after the linear matrix processing. The demosaicing processing (also referred to as equalization processing or synchronization processing) is the processing of interpolating the pixel value of a missing pixel, and is performed on the image after the gamma conversion processing. The missing pixel is a pixel with no pixel value because pixels in other colors are disposed in the image sensor 48. For example, since the B image is an image obtained by imaging the observation object with the B pixel, there is no pixel value in pixels at positions corresponding to the G pixel and the R pixel of the image sensor 48. In the demosaicing processing, the pixel values of the pixels at the positions of the G pixel and the R pixel of the image sensor 48 are generated by interpolating the B image. The YC conversion processing is the processing of converting the image after the demosaicing processing into a luminance image Y, a color difference image Cb, and a color difference image Cr.

The noise reduction unit 58 performs noise reduction processing using, for example, a moving average method, a median filter method, or the like on the luminance image Y, the color difference image Cb, and the color difference image Cr. The converting unit 59 re-converts the luminance image Y, color difference image Cb, and the color difference image Cr after the noise reduction processing into images in respective colors of BGR.

The image processing unit 61 has a normal processing unit 62 and a special processing unit 63. The normal processing unit 62 operates in the normal observation mode, and performs color conversion processing, color enhancement processing, and structure enhancement processing on the images in the respective colors of BGR to generate a normal image. In the color conversion processing, 3×3 matrix processing, gradation transformation processing, three-dimensional look-up table (LUT) processing, and the like are performed on the images in the respective colors of BGR. The color enhancement processing is the processing of enhancing the colors of an image, and the structure enhancement processing is the processing of enhancing, for example, the structure of an observation object, such as a blood vessel or a pit pattern. The display control unit 66 converts the normal image acquired from the normal processing unit 62 into a format suitable for display, and inputs the converted image to the monitor 18. Accordingly, the monitor 18 displays the normal image.

Figure 4:
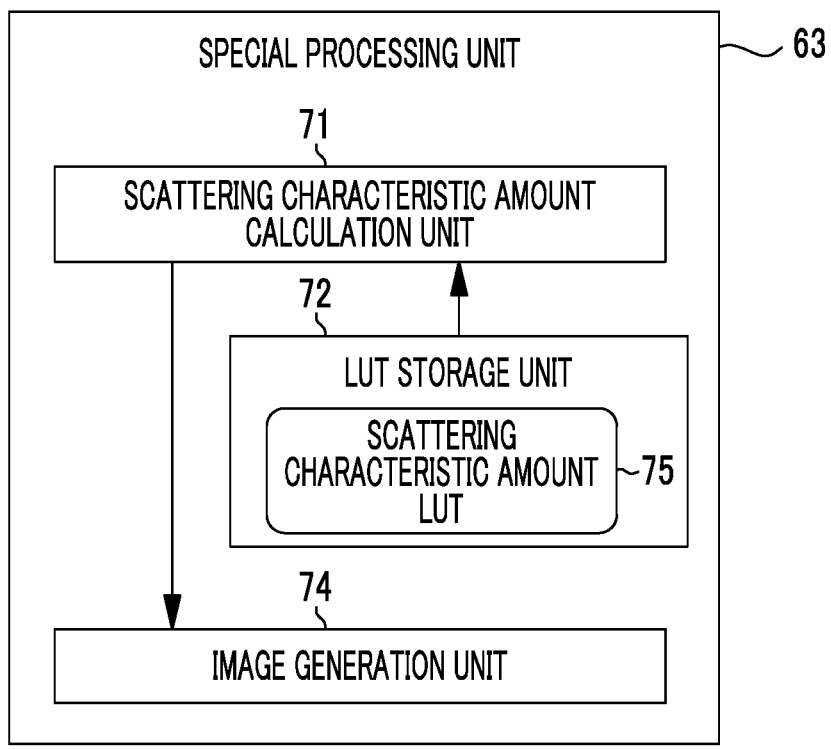
FIG. 4 is a block diagram of a special processing unit.

The special processing unit 63 operates in the scattering characteristic amount observation mode, calculates the scattering characteristic amount representing the scattering characteristic of the observation object, using the images of the three wavelength ranges obtained in the scattering characteristic amount observation mode, and generates the scattering characteristic amount image representing the distribution of the scattering characteristic amount. As illustrated in FIG. 4, the special processing unit 63 includes a scattering characteristic amount calculation unit 71, an LUT storage unit 72, and an image generation unit 74.

The scattering characteristic amount calculation unit 71 acquires color information from the images of the three wavelength ranges, and calculates the scattering characteristic amount representing the scattering characteristic of the observation object, using this color information. The color information is information on the balance between the colors of the observation object, for example, is the ratio or difference of the images of the three wavelength ranges. Additionally, the scattering characteristic amount calculation unit 71 acquires the color information for each pixel.

In the present embodiment, the scattering characteristic amount calculation unit 71 calculates a ratio G/B of the G image to the B image, and a ratio R/G of the R image to the G image for each pixel. That is, the color information acquired from the images of the three wavelength ranges are these two ratios G/B and R/G. Since the value of the ratio G/B mainly depends on blood amount and the scattering characteristic amount and the value of the ratio R/G mainly depends on the blood amount, the scattering characteristic amount that does not depend on the blood amount is obtained by using these two kinds of color information.

Additionally, by using the light beams of the equal absorption wavelength ranges in the scattering characteristic amount observation mode, there is also almost no influence of a quantitative difference (so-called oxygen saturation) between the oxyhemoglobin and the reduced hemoglobin. Hence, the scattering characteristic amount calculation unit 71 is able to calculate a precise scattering characteristic amount, using the two kinds of color information of the ratio G/B and the ratio R/G.

Figure 5:
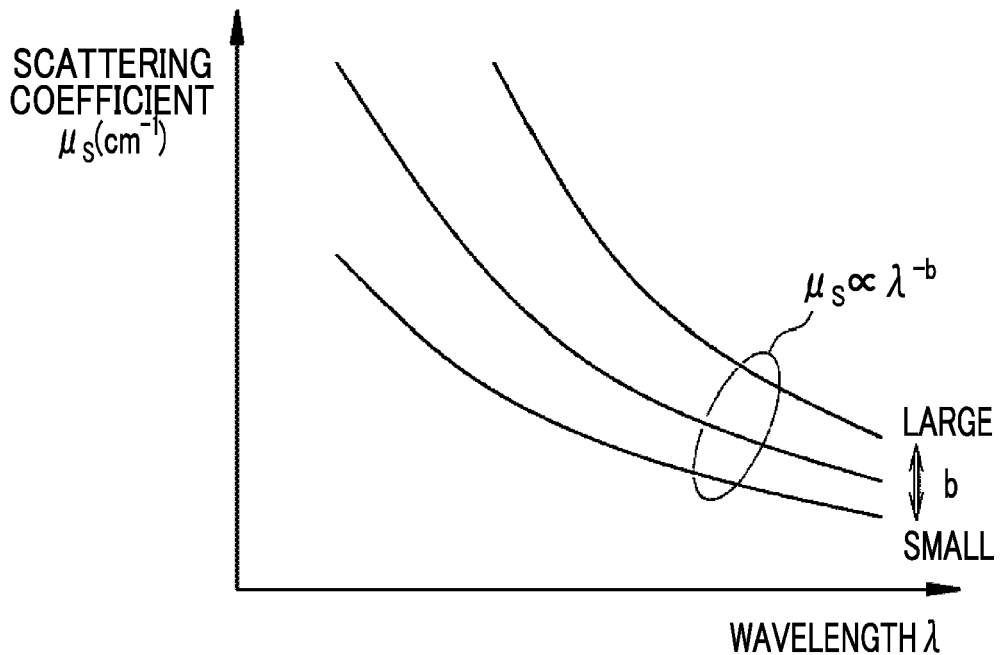
FIG. 5 is a graph illustrating the wavelength dependability of a scattering coefficient.

The scattering characteristic amount calculated by the scattering characteristic amount calculation unit 71 is a parameter representing the wavelength dependability of the scattering coefficient $\mu_s$, and as illustrated in FIG. 5, in a case where the observation object is uniform tissue, there is a relationship of "$\mu_s \propto \lambda^{-b}$" between the scattering coefficient $\mu_s$ and a wavelength $\lambda$. An "index b" of the relational expression is the "scattering characteristic amount" in the invention. Hereinafter, the index b is referred to as a scattering characteristic amount b.

The scattering characteristic amount b becomes larger as the size of scattering particles (tissue, structure, and the like that contribute to light scattering) included in the observation object is smaller. At a limit in which the scattering particles are regarded to be sufficiently small (Rayleigh scattering) as compared to the wavelength $\lambda$, the scattering characteristic amount b converges on b=4. Meanwhile, the index b becomes smaller as the scattering particles included in the observation object are larger and at a limit in which the scattering particles are regarded as from a size to be approximately equal to the wavelength $\lambda$ (Mie scattering) to a size to be sufficiently larger than the wavelength $\lambda$a (geometrical optical scattering), the scattering characteristic amount b gradually approaches b=0. However, in actual observation objects, such as a mucous membrane of an alimentary canal, the scattering characteristic amount b approximately converges on b=a value of about 0.6.

The scattering characteristic amount calculation unit 71 calculates the scattering characteristic amount with reference to a scattering characteristic amount LUT 75 stored in advance in the LUT storage unit 72. The scattering characteristic amount LUT 75 is a data structure representing a color information space where the color information acquired by the scattering characteristic amount calculation unit 71 is associated with the scattering characteristic amount b. The color information space represented by the scattering characteristic amount LUT 75 is formed with the color information acquired by the scattering characteristic amount calculation unit 71 as an axis, and a relationship between the scattering coefficient $\mu_s$ of the observation object and the scattering characteristic amount b is defined by "$\mu_s \propto \lambda^{-b}$".

Figure 6:
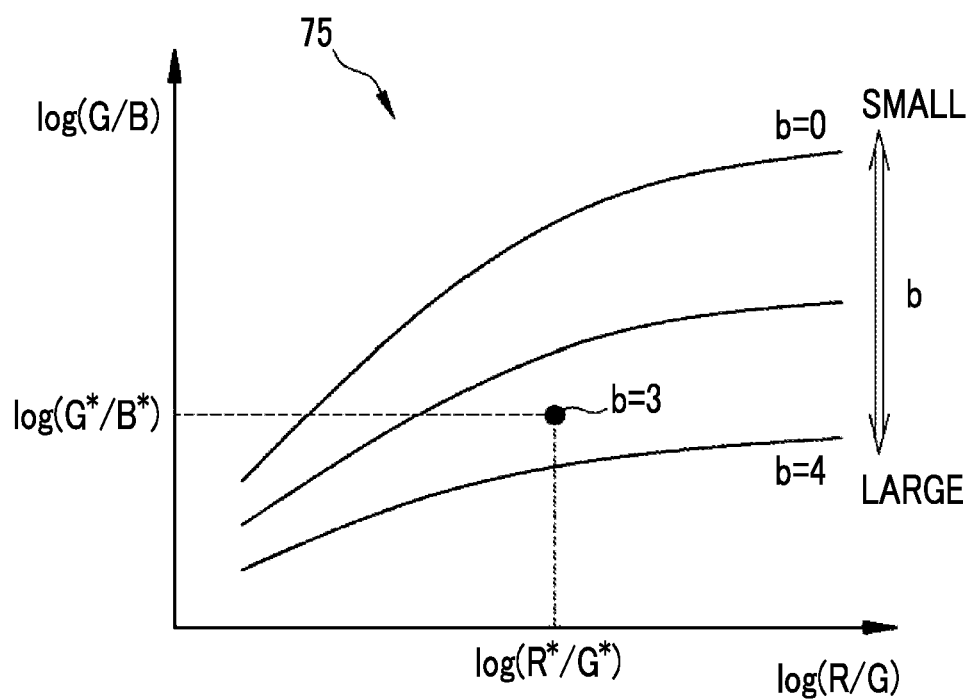
FIG. 6 is a graph illustrating the contents of a scattering characteristic amount LUT.

In the case of the present embodiment, the scattering characteristic amount calculation unit 71 acquires the ratio G/B and the ratio R/G as the color information. Thus, as illustrated in FIG. 6, the scattering characteristic amount LUT 75 is a two-dimensional map in which an isoplethic curve of the scattering characteristic amount b is defined in a space having the ratio R/G and the ratio G/B as axes. Additionally, the scattering characteristic amount LUT 75 stores this color information space in log scales. An isoplethic curve of the scattering characteristic amount b in a space having the ratio G/B and the ratio R/G as axes is obtained, for example, by physical simulation of the light scattering.

For example, in a case where the pixel value of a certain pixel representing the same portion of the observation object among the images of the three wavelength ranges is (B, G, R)=(B*, G*, R*), color information of this pixel is a ratio G*/B* and a ratio R*/G*. For this reason, the scattering characteristic amount calculation unit 71 refers to the scattering characteristic amount LUT 75, and obtains the value (in FIG. 6, b=3) of the scattering characteristic amount b corresponding to the ratio G*/B* and the ratio R*/G*.

The image generation unit 74 generates the scattering characteristic amount image representing the distribution of the scattering characteristic amount b calculated by the scattering characteristic amount calculation unit 71. Specifically, the image generation unit 74 generates an image (hereinafter referred to as a base image) 81 (refer to FIG. 9) that becomes a base of the scattering characteristic amount image. The base image 81 is generated by performing the color conversion processing, the color enhancement processing, and the structure enhancement processing on the images of the three wavelength ranges. That is, the base image 81 is a normal image generated using the images of the three wavelength ranges. In a case where the base image 81 is generated, the image generation unit 74 colors the base image 81, using the scattering characteristic amount b calculated by the scattering characteristic amount calculation unit 71, and generate a scattering characteristic amount image 82 (refer to FIG. 10) representing the distribution of the scattering characteristic amount b depending on colors. The image generation unit 74 modulates the color tone of the base image 81, for example, such that the blueness of a pixel having a larger scattering characteristic amount b is increased.

In the scattering characteristic amount observation mode, the display control unit 66 acquires the scattering characteristic amount image 82 from the image generation unit 74, and converts the acquired scattering characteristic amount image 82 into a format suitable for display to display the converted image on the monitor 18.

Next, a flow of operation of the endoscope system 10 in the scattering characteristic amount observation mode will be described along a flowchart illustrated in FIG. 7. In a case where the observation mode is switched to scattering characteristic amount observation mode, using the mode changeover switch 13a, the light source 20 sequentially emits the light beams of the three wavelength ranges of the blue wavelength range, the green wavelength range, and the red wavelength range, and the image sensor 48 images the observation object. Accordingly, the image acquisition unit 54 acquires the images of the three wavelength ranges (S11). As illustrated in FIG. 8, in the B image (B), the G image (G), and the R image (R) acquired by the image acquisition unit 54, undulations or the like of the observation object can be observed.

In a case where the image acquisition unit 54 acquires the images of the three wavelength ranges, the scattering characteristic amount calculation unit 71 acquires the color information from these images. That is, the scattering characteristic amount calculation unit 71 calculates the ratio G/B and the ratio R/G for each pixel (S12). Then, the scattering characteristic amount calculation unit 71 refers to the scattering characteristic amount LUT 75, and calculates the scattering characteristic amount b corresponding to the values of the ratio G/B and the ratio R/G of each pixel (S13).

Figure 9:
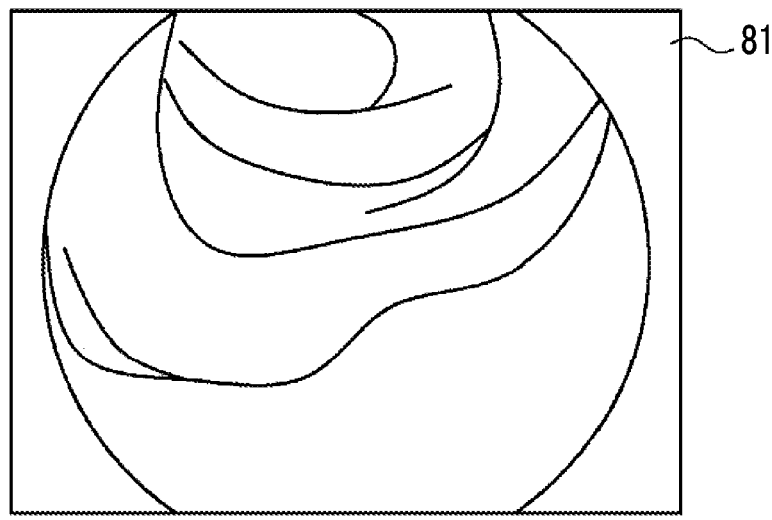
FIG. 9 is a base image.
Figure 10:
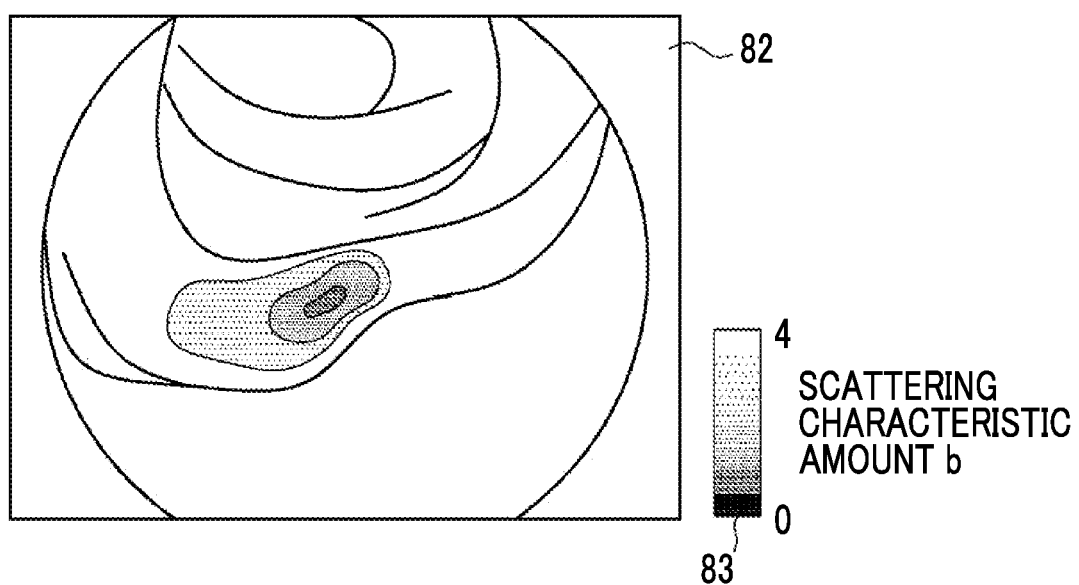
FIG. 10 is a scattering characteristic amount image.

On the other hand, in a case where the image acquisition unit 54 acquires the images of the three wavelength ranges, as illustrated in FIG. 9, the image generation unit 74 generates the base image 81, using these images (S14). According to the base image 81, the undulations or the like of the observation object can be observed in a natural tone substantially similarly to the normal image. Additionally, the image generation unit 74 generates the scattering characteristic amount image 82 by acquiring the scattering characteristic amount b from the scattering characteristic amount calculation unit 71, and as illustrated in FIG. 10, by coloring the generated base image 81 depending on the value of the scattering characteristic amount b (S15). The display control unit 66 displays the scattering characteristic amount image 82 on the monitor 18 together with color scales 83 showing a relationship between the value of the scattering characteristic amount b and the applied colors.

As described above, the endoscope system 10 generates and displays the scattering characteristic amount image 82 representing the distribution of the scattering characteristic amount b. The scattering characteristic amount image 82 is an image representing the distribution of the scattering characteristic amount b of the observation object in colors, and visualizes a tissue structure incapable of being observed in the B image, the G image, the R image and the base image 81, or an endoscopic image generated and displayed by a related-art endoscope system. Additionally, according to the scattering characteristic amount image 82, the denaturation of the tissue structure in which a lesion is not easily observed in a related-art endoscopic image in an initial stage or the like can also be observed in a case where there is a change in the scattering characteristic amount b to a normal portion. That is, according to the endoscope system 10, not only a lesion in which scattering particles following a specific scattering model are present but also various lesions can be discovered.

As can be seen from the method of calculating the scattering characteristic amount b, the scattering characteristic amount b can be calculated because the images of the three wavelength ranges of the blue wavelength range, the green wavelength range, and the red wavelength range are used. For example, even in a case where a plurality of images of the blue wavelength range, the scattering characteristic amount b of the invention cannot be calculated. Additionally, the scattering characteristic amount b fit for diagnosis is particularly easily calculated by using the equal absorption wavelength ranges as the three wavelength ranges of the blue wavelength range, the green wavelength range, and the red wavelength range.

In addition, the endoscope system 10 visualizes the distribution of the scattering characteristic amount b depending on the scattering characteristic amount image 82, and does not visualize a portion obtained by enhancing only a portion (for example, a portion of b=0) having a specific property regarding the light scattering. The process of enhancing only the portion having the specific property regarding the light scattering is the same as the process of enhancing a portion including scattering particles of a specific size. Hence, for example, in a system that enhances only the portion having the specific property regarding the light scattering, in the case of a lesion of a type in which the size of scattering particles vary depending on the progress of a disease state, the lesion cannot be caught until the scattering particles have a specific size. Meanwhile, in the endoscope system 10, the scattering characteristic amount b is calculated and the distribution thereof is imaged. Thus, even in the lesion of the type which the size of the scattering particles vary depending on the progress of the disease state, the lesion can be caught in a case where a change occurs in the size of the scattering particles and there is a change in the scattering characteristic amount b.

In the above first embodiment, the scattering characteristic amount image 82 is generated by coloring the base image 81 depending on the value of the scattering characteristic amount b. However, the scattering characteristic amount image 82 may be generated by setting a range to the scattering characteristic amount b and coloring a portion having a value within the range to which the scattering characteristic amount b is set. For example, only pixels that satisfies 1<b<3 may be colored.

Additionally, in the above first embodiment, as the wavelength ranges of the light beams to be used in the scattering characteristic amount observation mode, the blue wavelength range is 450±10 nm, the green wavelength range is 540±10 nm, and the red wavelength range is 620±10 nm. However, the respective wavelength ranges of the light beams of the three wavelength ranges to be used in the scattering characteristic amount observation mode may be other wavelength ranges.

For example, in the blue wavelength range, there are also equal absorption wavelength ranges in the vicinity of 390±10 nm, 420±10 nm, and 500±10 nm, respectively, (refer to FIG. 3). For this reason, in addition to the wavelength range of 450±10 nm, these respective wavelength ranges can be used as the light beam of the blue wavelength range in the scattering characteristic amount observation mode. However, since fine tissue and structure, such as blood vessels or pit patterns, can be observed well in a shorter wavelength range particularly in the blue wavelength range, it becomes difficult to regard the observation object as uniform tissue. Since a relationship in which the scattering coefficient $\mu_s$ satisfies "$\mu_s \propto \lambda^{-b}$" with the wavelength $\lambda$ is a case where the observation object is near the uniform tissue, there is a case where an error may become larger as the wavelength range of the light beam of the blue wavelength range is shorter. Additionally, the vicinity of 500±10 nm is close to the green wavelength range, and in a case where this equal absorption wavelength range is used, it is relatively difficult to catch a change in the value of the ratio G/B. For this reason, the equal absorption wavelength range in the vicinity of 450±10 nm is most suitable as the light beam of the blue wavelength range to be used in the scattering characteristic amount observation mode.

Since the green wavelength range also include equal absorption wavelength ranges, such as 520±10 nm and 570±10 nm, light beams of these absorption wavelength ranges can be used as the light beam of the green wavelength range in the scattering characteristic amount observation mode. Additionally, in the red wavelength range, the light absorption coefficients of the oxyhemoglobin and the reduced hemoglobin are small. Thus, any wavelength ranges can be used as the light beam of the red wavelength range in the scattering characteristic amount observation mode. However, although depending on a part or the like of the observation object, it is better to avoid use of a wavelength range in which light emission, such as fluorescence from the observation object, increases.

In addition, in the above first embodiment, the scattering characteristic amount image 82 is displayed on the monitor 18. However, the scattering characteristic amount image 82 and the base image 81 (or the normal image generated in the normal observation mode) may be displayed side by side on the monitor 18. Additionally, the display of the scattering characteristic amount image 82 and the display of the base image 81 (normal image) may be arbitrarily switched therebetween.

Second Embodiment

In the above first embodiment, the scattering characteristic amount image 82 is generated by coloring the base image 81, using the scattering characteristic amount b. However, in a case where the scattering characteristic amount image 82 is generated, the base image 81 may be colored by adding biological information or the like other than the scattering characteristic amount b.

For example, the scattering characteristic amount image 82 can be generated by calculating the oxygen saturation of the observation object and taking not only the scattering characteristic amount b but also the value of the oxygen saturation into consideration. In this case, the light source 20 emits a light beam of a fourth wavelength range for measuring the oxygen saturation of the observation object other than the light beams of the three wavelength ranges of the blue wavelength range, the green wavelength range, and the red wavelength range of the first embodiment. The three wavelength ranges of the blue wavelength range, the green wavelength range, and the red wavelength range are the equal absorption wavelength ranges, whereas the fourth wavelength range is a wavelength range having a difference between the light absorption coefficient of the oxyhemoglobin included in the observation object and the light absorption coefficient of the reduced hemoglobin included in the observation object. In the present embodiment, the fourth wavelength range is a wavelength range in which the difference between light absorption coefficients $\mu_a$ of the oxyhemoglobin and the reduced hemoglobin becomes extremely large, for example, the blue wavelength range, such as 430±10 nm or 470±10 nm, (refer to FIG. 3). In the present embodiment, the light beam of the wavelength range of 470±10 nm is used as the light beam of the fourth wavelength range. For this reason, in addition to the image (B image) of the blue wavelength range, the image (G image) of the green wavelength range, and the image (R image) of the red wavelength range, the image acquisition unit 54 acquires an image (hereinafter referred to as $B_{470}$ image for distinction from the B image) of the fourth wavelength range.

Figure 11:
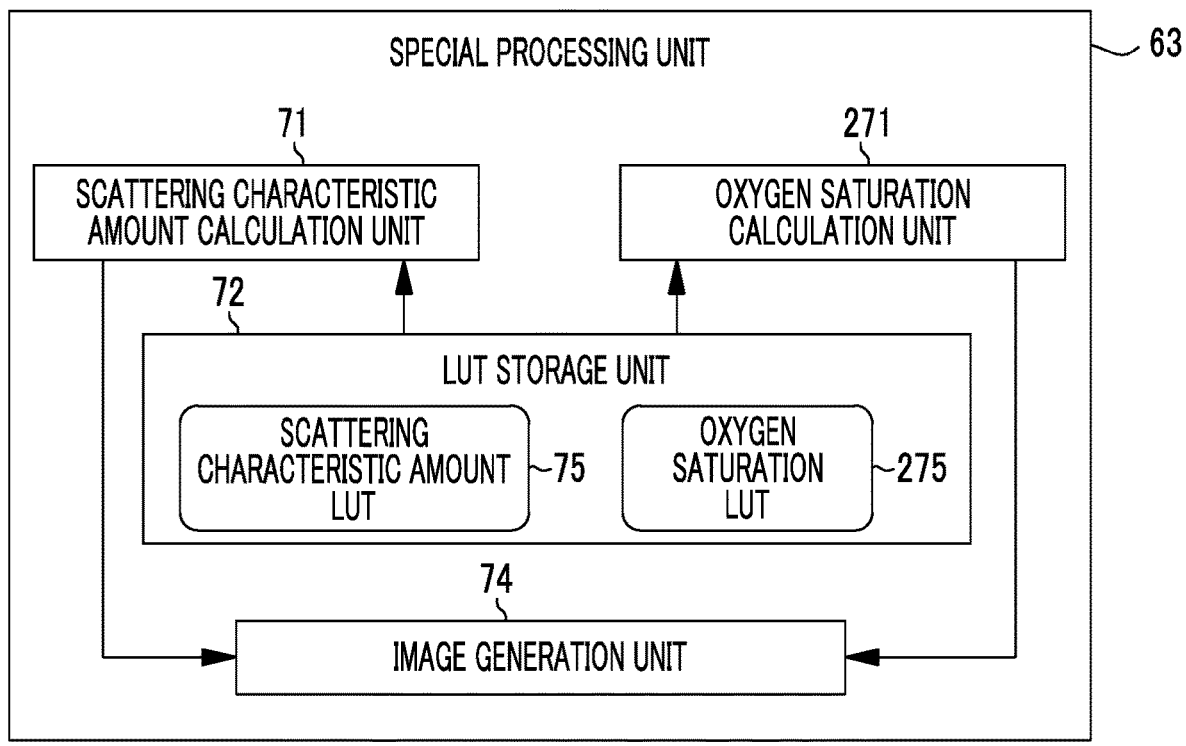
FIG. 11 is a block diagram of a special processing unit 63 of a second embodiment.

Also, as illustrated in FIG. 11, the special processing unit 63 includes an oxygen saturation calculation unit 271 in addition to the scattering characteristic amount calculation unit 71 and the image generation unit 74. Additionally, in addition to the scattering characteristic amount LUT 75, an oxygen saturation LUT 275 is stored in advance in the LUT storage unit 72.

The oxygen saturation calculation unit 271 calculates the oxygen saturation of the observation object, using the image acquired by the image acquisition unit 54. In a case where the oxygen saturation is calculated, the oxygen saturation calculation unit 271 first acquires the color information from the image acquired by the image acquisition unit 54. Specifically, the oxygen saturation calculation unit 271 calculates a ratio $B_{470}/G$ of the $B_{470}$ image to the G image and the ratio R/G of the R image to the G image for each pixel. The ratio $B_{470}/G$ mainly depends on the oxygen saturation and the blood amount. Additionally, as mentioned above also in the first embodiment, the ratio R/G depends on the blood amount. Hence, the oxygen saturation that does not depend on the blood amount can be calculated by using two kinds of color information of the ratio $B_{470}/G$ and the ratio R/G.

Figure 12:
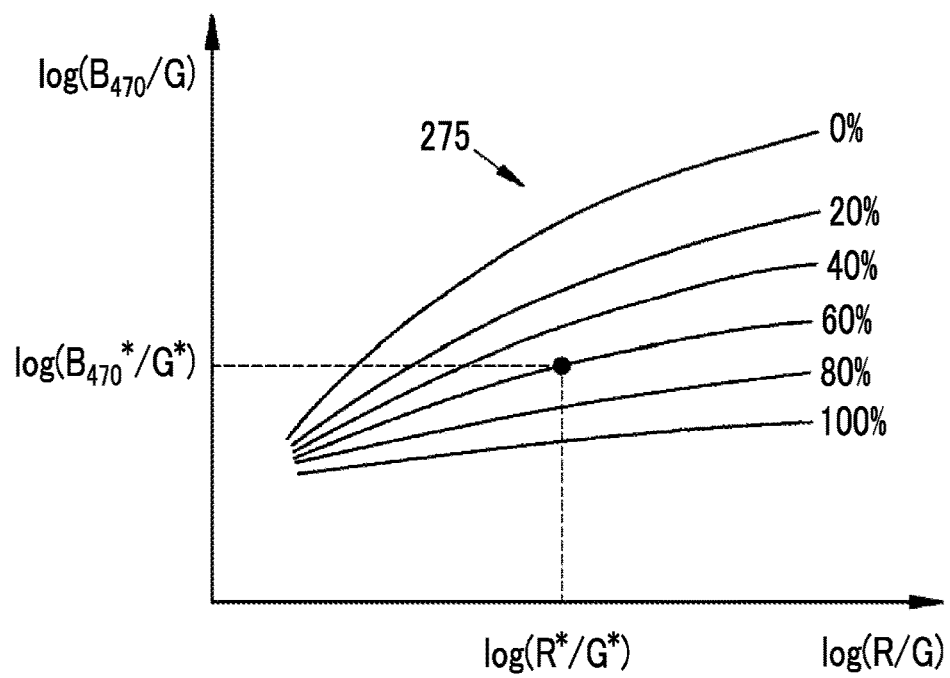
FIG. 12 is a graph illustrating the contents of oxygen saturation LUT.

The oxygen saturation calculation unit 271 calculates the oxygen saturation with reference to the oxygen saturation LUT 275 in a case where the ratio $B_{470}/G$ and the ratio R/G are calculated as described above. The oxygen saturation LUT 275 is a data structure representing a color information space in which the color information acquired by the oxygen saturation calculation unit 271 is associated with the oxygen saturation. The color information space represented by the oxygen saturation LUT 275 is a map in which an isoplethic curve of the oxygen saturation is defined as a space having the color information acquired by the oxygen saturation calculation unit 271 as axes. In the present embodiment, the oxygen saturation calculation unit 271 acquires the two kinds of color information of the ratio $B_{470}/G$ and the ratio R/G. Thus, as illustrated in FIG. 12, the oxygen saturation LUT 275 is a two-dimensional map in which the isoplethic curve of the oxygen saturation is defined within a two-dimensional space having the ratio $B_{470}/G$ and the ratio R/G as axes. In addition, the oxygen saturation LUT 275 stores this color information space in log scales. Additionally, the isoplethic curve of the oxygen saturation to the color information (the ratio $B_{470}/G$ and the ratio R/G) is obtained, for example, by physical simulation of light scattering.

In a case where the pixel value of a certain pixel representing the same portion of the observation object among the B image, the G image, the R image, and the $B_{470}$ image is (B, G, R, $B_{470}$)=(B*, G*, R*, $B_{470}$*), color information of this pixel is a ratio $B_{470}$*/G* and a ratio R*/G*. For this reason, the oxygen saturation calculation unit 271 refers to the oxygen saturation LUT 275, and obtains the value (in FIG. 12, "60%") of the oxygen saturation corresponding to the ratio $B_{470}$*/G* and the ratio R*/G*.

In parallel with the calculation of the oxygen saturation by the oxygen saturation calculation unit 271, the scattering characteristic amount calculation unit 71 calculates the scattering characteristic amount b for each pixel. The fact that the scattering characteristic amount calculation unit 71 acquires the color information (the ratio G/B and the ratio R/G) from the B image, the G image, and the R image, and calculates the scattering characteristic amount b with reference to the scattering characteristic amount LUT 75 is the same as that of the first embodiment.

The image generation unit 74 acquires the scattering characteristic amount b from the scattering characteristic amount calculation unit 71, and acquires the oxygen saturation from the oxygen saturation calculation unit 271, and generates the scattering characteristic amount image 282 (refer to FIG. 13) using these. Specifically, the image generation unit 74 first generates the base image 81, using B image, G image, and R image, similarly to the first embodiment (refer to FIG. 9).

Figure 13:
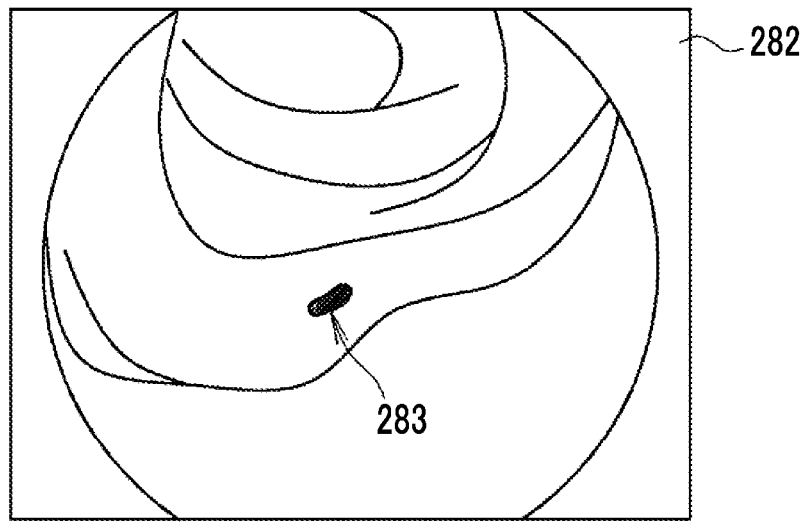
FIG. 13 is a scattering characteristic amount image of the second embodiment.

Then, the image generation unit 74 sets ranges to the scattering characteristic amount b and the oxygen saturation, respectively, and colors a portion 283 with respect to the base image 81 within the range where the scattering characteristic amount b is set and the range where the oxygen saturation is set. Accordingly, as illustrated in FIG. 13, the image generation unit 74 generates the scattering characteristic amount image 282 in which the portion 283 within the range where the scattering characteristic amount b is set and the range where the oxygen saturation is set is enhanced. For this reason, in addition to the distribution of the scattering characteristic amount b, the scattering characteristic amount image 282 also represents the distribution of the oxygen saturation.

The ranges of the scattering characteristic amount b and the oxygen saturation are set, for example, depending threshold values determined in advance by setting input or the like. In the present embodiment, the image generation unit 74 determines a first threshold value Th1 (for example, Th1=3.5) with respect to the scattering characteristic amount b, and sets a second threshold value Th2 (for example, Th2=60%) with respect to the oxygen saturation. Then, the scattering characteristic amount b of each pixel is compared with the first threshold value Th1, the oxygen saturation of each pixel is compared with the second threshold value Th2, and the portion 283 in which the scattering characteristic amount b is equal to or less than the first threshold value Th1 (equal to or more than b=0) and the oxygen saturation is equal to or less than the second threshold value Th2 (equal to or more than 0%) is enhanced.

The portion in which the scattering characteristic amount b is equal to or less than the first threshold value Th1 is enhanced because, although depending on the type of lesion or the like, the scattering characteristic amount b of a lesioned portion becomes an approximately small value with respect to the scattering characteristic amount b of the normal portion. Similarly, the portion in which the oxygen saturation is equal to or less than the second threshold value Th2 is enhanced because the oxygen saturation of the lesioned portion becomes approximately small with respect to the oxygen saturation (about 70%) of the normal portion. Hence, the portion 283 in which the scattering characteristic amount b is equal to or less than the first threshold value Th1 and the oxygen saturation is equal to or less than the second threshold value Th2 is a portion with a particularly high possibility of being a lesion. For this reason, the scattering characteristic amount image 282 can pinpoint a portion with a high accuracy of a lesion more clearly than the scattering characteristic amount image 82 of the first embodiment.

In addition, in the above second embodiment, an upper limit is set with respect to the scattering characteristic amount b by the first threshold value Th1 and a natural lower limit value (b=0) of the scattering characteristic amount b is set as a lower limit. However, the lower limit can also be set explicitly. In this case, the above first threshold value Th1 becomes a group of an upper limit value and a lower limit value of a range to be set to the scattering characteristic amount b. For example, in a case where the first threshold value Th1 is a group of an upper limit value U1 and a lower limit value L1, a portion in which the scattering characteristic amount b is equal to or less than the upper limit value U1 and equal to or more than the lower limit value L1 can be a candidate of a portion to be enhanced.

Similarly, in the above second embodiment, an upper limit is set with respect to the oxygen saturation by the second threshold value Th2 and a natural lower limit value (0%) of the oxygen saturation is set as a lower limit. However, the lower limit can also be set explicitly. For example, in a case where the second threshold value Th2 is a group of an upper limit value U2 and a lower limit value L2 for the oxygen saturation, a portion in which the oxygen saturation is equal to or less than the upper limit value U2 and equal to or more than the lower limit value L2 can be a candidate of a portion to be enhanced.

The scattering characteristic amount image 282 of the above second embodiment colors the portion 283 within the range where the scattering characteristic amount b is set and the range where the oxygen saturation is set. However, since a difference in the presence/absence of coloring occurs depending on at least the value of the scattering characteristic amount b, the scattering characteristic amount image 282 is an image representing the distribution of the scattering characteristic amount b.

In addition, the color or the like of the portion 283 to be colored can be set arbitrarily. That is, the portion 283 to be colored is selected in accordance with the above second embodiment, and the selected portion 283 is colored by any methods. As for the portion 283 to be colored, the entire portion 283 may be colored in monochrome, such as blue. However, it is preferable that the color or the like of the portion 283 is set depending on the scattering characteristic amount b, the oxygen saturation, or the values of the scattering characteristic amount b and the oxygen saturation. For example, in a case where the entire portion 283 is colored in the same color, the color can be determined depending on the scattering characteristic amount b, the oxygen saturation, or the values of the scattering characteristic amount b and the oxygen saturation. For example, the portion 283 is colored in blue in a case where the statistic amount (an average value, a maximum value, a minimum value, a median value, or the like) of the scattering characteristic amount b of the portion 283 is equal to or less than a predetermined value, and the portion 283 is colored in brighter blue than in a case where the statistic amount of the scattering characteristic amount b of the portion 283 is larger than a predetermined position.

Additionally, what color the portion 283 is colored in may be changed for each pixel in the portion 283 depending on the scattering characteristic amount b, the oxygen saturation, or the values of the scattering characteristic amount b and the oxygen saturation. For example, each of pixels in which the scattering characteristic amount b is equal to or less than 1 is colored in blue, and each of pixels in which the scattering characteristic amount b is equal to or less than 2 greater than 1 is colored in green.

Figure 14:
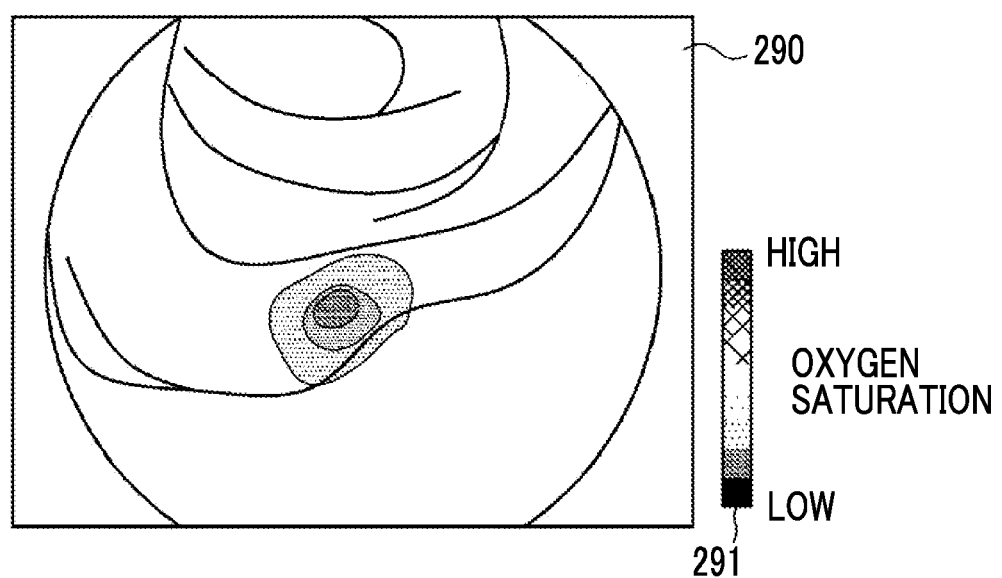
FIG. 14 is an oxygen saturation image.

In the above second embodiment, the image generation unit 74 generates the scattering characteristic amount image 282. However, the image generation unit 74 of the second embodiment can generate the same scattering characteristic amount image 82 as the first embodiment or an oxygen saturation image 290 representing the oxygen saturation of the observation object. As illustrated in FIG. 14, the oxygen saturation image 290 is an image obtained by coloring the base image 81 depending on the oxygen saturation. Color scales 291 show a correspondence relationship between the color of the oxygen saturation image 290, and the value of the oxygen saturation. The display control unit 66 can display two or more of the scattering characteristic amount image 82, the scattering characteristic amount image 282, and the oxygen saturation image 290 side by side on the monitor 18. Moreover, the display control unit 66 can switch and display the scattering characteristic amount image 82, the scattering characteristic amount image 282, and the oxygen saturation image 290 in accordance with operation.

In addition, in the above first and second embodiments, in the scattering characteristic amount observation mode, the observation object is imaged by sequentially radiating the light beams of the three wavelength ranges of the blue wavelength range, the green wavelength range, and the red wavelength range. However, in a case where the image sensor 48 is a color sensor, the B image, the G image, and the R image can be simultaneously obtained by simultaneously radiating these light beams.

Figure 15:
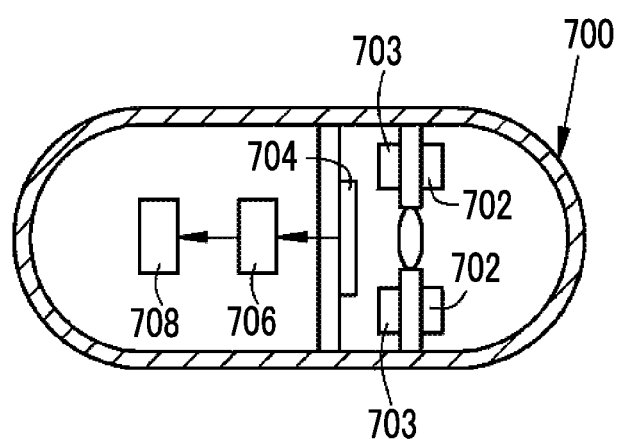
FIG. 15 is a schematic view of a capsule endoscope.

In addition, in the above first and second embodiments, the invention is carried out by the endoscope system 10 that performs observation by inserting the endoscope 12 provided with the image sensor 48 into a subject. However, a capsule endoscope system is also suitable for the invention. For example, as illustrated in FIG. 15, the capsule endoscope system has at least a capsule endoscope 700 and a processor device (not illustrated).

A capsule endoscope 700 includes a light source 702, a control unit 703, an image sensor 704, an image processing unit 706, and a transmission/reception antenna 708. The light source 702 corresponds to the light source 20. The control unit 703 functions similarly to the light source control unit 22 and the control unit 52. Additionally, the control unit 703 is capable of wirelessly communicating with a processor device of a capsule endoscope system by the transmission/reception antenna 708. Although the processor device of the capsule endoscope system is substantially the same as that of the above processor device 16 of the first and second embodiments, the image processing unit 706 corresponding to the image acquisition unit 54 and the image processing unit 61 is provided in the capsule endoscope 700, and the generated scattering characteristic amount image 82 or the like is transmitted to the processor device via the transmission/reception antenna 708. The image sensor 704 is configured similarly to the image sensor 48.

EXPLANATION OF REFERENCES

10: endoscope system
16: processor device
54: image acquisition unit
61: image processing unit
62: normal processing unit
63: special processing unit
71: scattering characteristic amount calculation unit
72: LUT storage unit
74: image generation unit
75: scattering characteristic amount LUT
271: oxygen saturation calculation unit
275: oxygen saturation LUT
700: capsule endoscope

What is claimed is:

1. A processor device comprising:
a processor, configured to:
acquire images of three wavelength ranges of a blue wavelength range, a green wavelength range, and a red wavelength range;
acquire color information from the images of the three wavelength ranges;
calculate a scattering characteristic amount representing a scattering characteristic of an observation object using the color information; and
generate a scattering characteristic amount image representing a distribution of the scattering characteristic amount.

2. The processor device according to claim 1,
wherein the blue wavelength range, the green wavelength range, and the red wavelength range include equal absorption wavelength ranges in which light absorption coefficients of oxyhemoglobin and reduced hemoglobin are equal to each other.

3. The processor device according to claim 1,
wherein the processor calculates a ratio or difference between the images of the three wavelength ranges as the color information, and calculates the scattering characteristic amount, using the calculated ratio or difference.

4. The processor device according to claim 2,
wherein the processor calculates a ratio or difference between the images of the three wavelength ranges as the color information, and calculates the scattering characteristic amount, using the calculated ratio or difference.

5. The processor device according to claim 3,
wherein the processor calculates the scattering characteristic amount, using the ratio or difference between the image of the red wavelength range and the image of the green wavelength range, and the ratio or difference between the image of the green wavelength range and the image of the blue wavelength range.

6. The processor device according to claim 4,
wherein the processor calculates the scattering characteristic amount, using the ratio or difference between the image of the red wavelength range and the image of the green wavelength range, and the ratio or difference between the image of the green wavelength range and the image of the blue wavelength range.

7. The processor device according to claim 1,
wherein the processor calculates a parameter representing wavelength dependability of a scattering coefficient of the observation object as the scattering characteristic amount.

8. The processor device according to claim 2,
wherein the processor calculates a parameter representing wavelength dependability of a scattering coefficient of the observation object as the scattering characteristic amount.

9. The processor device according to claim 3,
wherein the processor calculates a parameter representing wavelength dependability of a scattering coefficient of the observation object as the scattering characteristic amount.

10. The processor device according to claim 4,
wherein the processor calculates a parameter representing wavelength dependability of a scattering coefficient of the observation object as the scattering characteristic amount.

11. The processor device according to claim 5,
wherein the processor calculates a parameter representing wavelength dependability of a scattering coefficient of the observation object as the scattering characteristic amount.

12. The processor device according to claim 7,
wherein the processor calculates a scattering characteristic amount "b" corresponding to the color information in a color information space which is formed with the color information as axes and in which a relationship among a wavelength "$\lambda$", a scattering coefficient $\mu_s$, of the observation object, and the scattering characteristic amount "b" is defined by $$\mu_s \propto \lambda^{-b}. \qquad \text{Expression 1:}$$

13. The processor device according to claim 1,
wherein the processor acquires an image of a fourth wavelength range having a difference between the light absorption coefficient of the hemoglobin and the light absorption coefficient of the reduced hemoglobin as compared to the three wavelength ranges,
wherein the processor further calculates an oxygen saturation of the observation object, using the image of the fourth wavelength range, and
generates the scattering characteristic amount image representing a distribution of the oxygen saturation as well as the distribution of the scattering characteristic amount.

14. The processor device according to claim 13,
wherein the processor sets ranges to the scattering characteristic amount and the oxygen saturation, respectively, and generates the scattering characteristic amount image in which a portion which is present within a range where the scattering characteristic amount is set and a range where the oxygen saturation is set is enhanced.

15. The processor device according to claim 14,
wherein the processor compares the scattering characteristic amount with a first threshold value, and generates the scattering characteristic amount image in which a portion in which the scattering characteristic amount is equal to or less than the first threshold value is enhanced.

16. The processor device according to claim 14,
wherein the processor compares the oxygen saturation with a second threshold value, and generates the scattering characteristic amount image in which a portion in which the oxygen saturation is equal to or less than the second threshold value is enhanced.

17. An endoscope system comprising:
a processor device comprising:
a processor, configured to:
acquire images of three wavelength ranges of a blue wavelength range, a green wavelength range, and a red wavelength range;
acquire color information from the images of the three wavelength ranges;
calculate a scattering characteristic amount representing a scattering characteristic of an observation object using the color information; and
generate a scattering characteristic amount image representing a distribution of the scattering characteristic amount.

18. An image processing method for a processor device according to claim 1 comprising:
acquiring images of three wavelength ranges of a blue wavelength range, a green wavelength range, and a red wavelength range;
acquiring color information from the images of the three wavelength ranges,
calculating a scattering characteristic amount representing a scattering characteristic of an observation object using the color information; and
generating a scattering characteristic amount image representing a distribution of the scattering characteristic amount.

* * * * *